United States Patent [19]

Warriner

[11] Plant 5,001

[45] Mar. 22, 1983

[54] ROSE PLANT—74-2681

[75] Inventor: William A. Warriner, Tustin, Calif.

[73] Assignee: Jackson & Perkins Company, Medford, Oreg.

[21] Appl. No.: 299,024

[22] Filed: Sep. 3, 1981

[51] Int. Cl.[3] ..... A01H 5/00
[52] U.S. Cl. ..... Plt./24
[58] Field of Search ..... Plt./24

*Primary Examiner*—Robert E. Bagwill
*Attorney, Agent, or Firm*—Klarquist, Sparkman, Campbell, Leigh, Whinston & Dellett

[57] ABSTRACT

A floribunda rose variety having a plant attaining three feet in height and three feet in diameter after two growing seasons; shiny foliage; yellow blooms borne singly and in clusters with 20–25 petals; little fragrance; and numerous long thorns.

1 Drawing Figure

1

This present invention relates to a new and distinct variety of rose plant of the floribunda class which was originated by me by crossing the variety Sunsprite, U.S. Plant Pat. No. 3,509, with an unnamed variety.

The primary objective of this breeding was to produce a new rose variety of a compact, dense habit, abundantly producing yellow flowers on a plant with foliage resistant to the diseases rose mildew and rose blackspot. This objective was substantially achieved along with other desirable improvements as evidenced by the following unique combination of characteristics which are outstanding in the new variety and which distinguish it from its parents as well as from all other varieties of which I am aware:

1. A plant normally growing in two seasons to a height of 3 feet and diameter of 3 feet at Irvine, Calif.
2. Shiny foliage resistant to a high degree to rose powdery mildew and rose blackspot.
3. Blooms borne singly and in clusters of yellow color with 20 to 25 petals.
4. Very little fragrance.
5. Numerous long thorns, pointing slightly downward.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:
- *Seed parent.*—Sunsprite, U.S. Plant Pat. No. 3,509.
- *Pollen parent.*—Unnamed variety.

Classification:
- *Botanical.*—Rosa hybrid.
- *Commercial.*—Floribunda.

2

FLOWER

Observations made from specimens grown at Irvine, Calif., in December 1980.

Blooming habit: Recurrent, continuous.

Bud:
- *Size.*—$\frac{3}{4}$" when petals start to unfurl.
- *Form.*—Pointed ovoid, broad base.
- *Color.*—When sepals first divide, near yellow 13A tipped with Orange 30C; when half blown, upper side of petals near Yellow 13A; lower side of petals same Yellow 13A.
- *Sepals.*—Color: Outer surface Green 138A, lighter near edges to 138B, sometimes with brown shading. Three appendaged sepals lightly appendaged. Two unappendaged sepals hairy edge and glandular.
- *Receptacle.*—Color: Green 138A. Shape: funnel. Size: large, broad. Surface: nearly smooth.
- *Peduncle.*—Length: short. Surface: having minute, fine pubescence. Color: medium green. Strength: stiff, bending, slender.
- *Opening.*—Petals fold outward with slight curling of petals.

Bloom:
- *Size.*—Large. Average open size 4".
- *Borne.*—Singly or in clusters. If in clusters, flat.
- *Stems.*—Short.
- *Form.*—When first open, high center. Permanence: Retains its form to the end; flattens, in fully open flower.
- *Petalage.*—Number of petals under normal conditions: 20–25.
- *Color.*—Center of flower: Upper side of petals Yellow 13A. Reverse side of petals Yellow 13A. Base of petals deeper Yellow 15A. General tonality from a distance Yellow 13A.
- *Variegations.*—None.
- *Discoloration.*—General tonality at end of first day Yellow 13A; third day much lighter Yellow 10C to D.
- *Fragrance.*—Slight.

Petals:
- *Texture.*—Thin.
- *Shape.*—Obovate.
- *Form.*—Tips slightly recurved.
- *Arrangement.*—Informal. Petaloids in center, few.

*Persistence.*—Drop off cleanly.
*Lastingness.*—On the plant, fair. As cut flower, fair.

Reproductive parts:
*Anthers.*—Large. Color, yellow. Arrangement: regular around styles.
*Filaments.*—Color: Yellow.
*Pollen.*—Gold yellow.
*Styles.*—Color: reddish.
*Stigmas.*—Color: Buff, yellow.

PLANT

Form: Bush.

Growth: Vigorous, branching. Normal size approximately 3 feet high and 3 feet wide.

Foliage: Number of leaflets on normal mid-stem leaves: 5–7.
*Size.*—Medium.
*Quantity.*—Normal.
*Color.*—New foliage: Near greyed Purple 187B. Old foliage: Near green 126A but varying according to soil fertility.

Leaflets:
*Shape.*—Oval pointed.
*Texture.*—Upper side, glossy.
*Edge.*—Serrated.

*Serration.*—Single, large.
*Petiole.*—Rachis: Color, green. Underside: prickles.
*Stipules.*—Long, bearded.
*Disease resistance.*—Very resistant to rose powdery mildew and rose blackspot at Irvine, Calif.

Wood:
*New wood.*—Color: light green. Bark: Smooth.
*Old wood.*—Color: Green. Bark: Smooth.

Prickles:
*Quantity.*—On main stalks from base, many. On laterals from stalk, many.
*Form.*—Long, hooked slightly downward.
*Color when young.*—Red.
*Position.*—Irregular.

Small prickles:
*Quantity.*—On main stalks, none. On laterals, none.

I claim:

1. A new and distinct variety of rose plant of the floribunda class, substantially as herein shown and described, characterized particularly as to novelty by the unique combination of its compact plant, glossy, disease resistant foliage, yellow blooms, light fragrance and numerous, large prickles.

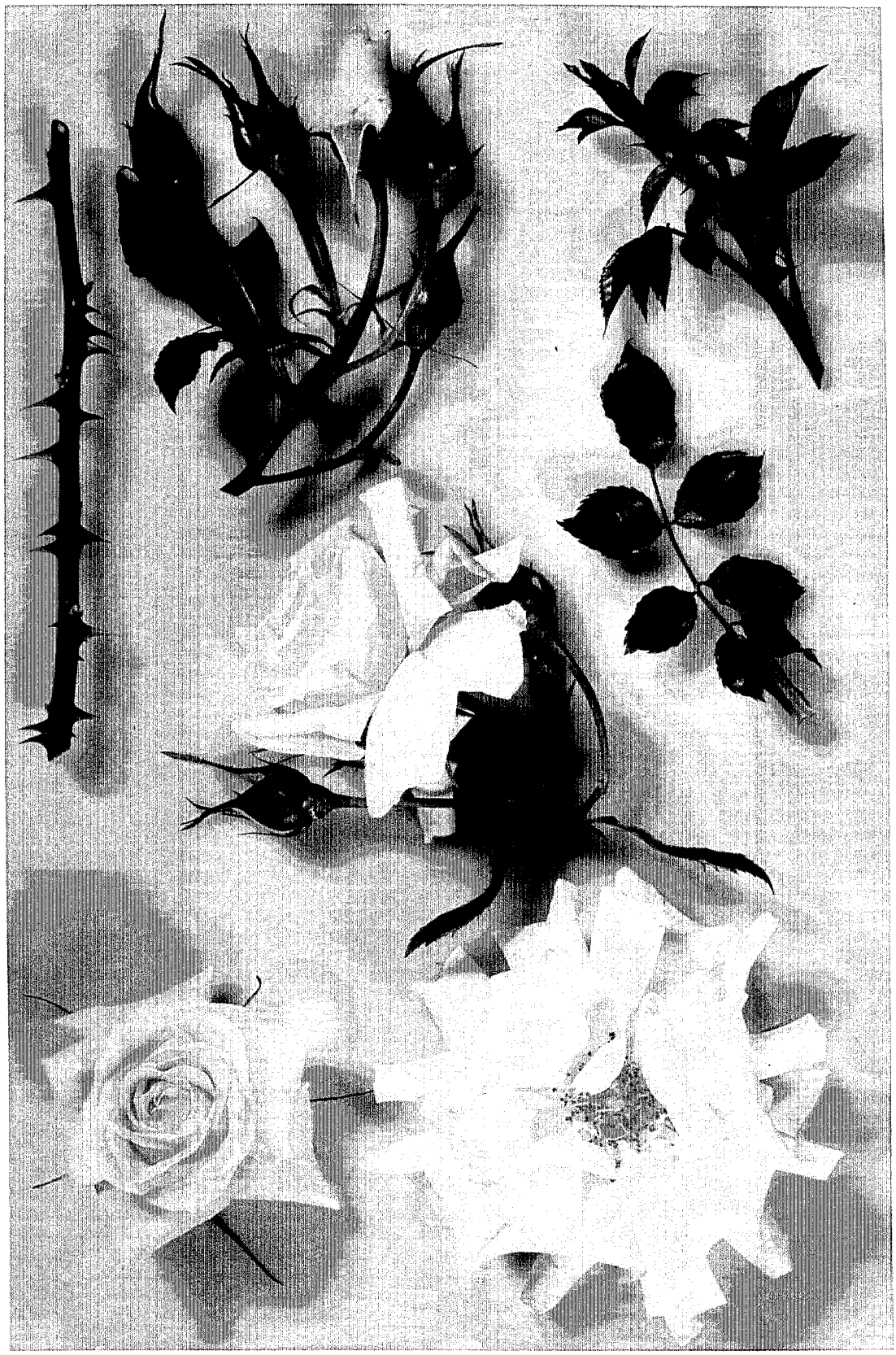

* * * * *